United States Patent [19]

Saito

[11] Patent Number: 5,359,639
[45] Date of Patent: Oct. 25, 1994

[54] METHOD AND APPARATUS FOR COMPUTERIZED TOMOGRAPHY

[75] Inventor: Masahiro Saito, Kyoto, Japan

[73] Assignee: Shimadzu Corporation, Kyoto, Japan

[21] Appl. No.: 90,933

[22] Filed: Jul. 14, 1993

[30] Foreign Application Priority Data

Jul. 16, 1992 [JP] Japan .................. 4-213597

[51] Int. Cl.⁵ ............................. G21K 1/04
[52] U.S. Cl. ...................... 378/4; 378/146; 378/20
[58] Field of Search .............. 378/145, 146, 147, D4, 378/148, 149, 150, 151, 21, 4, 20

[56] References Cited

U.S. PATENT DOCUMENTS

| | | | |
|---|---|---|---|
| 4,789,929 | 12/1988 | Nishimura et al. | 364/413.15 |
| 5,054,041 | 10/1991 | Hampel | 378/4 |
| 5,090,037 | 2/1992 | Toth et al. | 378/4 |

FOREIGN PATENT DOCUMENTS

0487245A1 11/1991 European Pat. Off. .
61-109551 5/1986 Japan .

OTHER PUBLICATIONS

Patent Abstract of Japan; JP-A-56163468; "Radiation Type Tomographic Apparatus"; vol. 6, No. 46, p. 107; Mar. 24, 1982.

*Primary Examiner*—David P. Porta
*Assistant Examiner*—Don Wong
*Attorney, Agent, or Firm*—Nikaido, Marmelstein, Murray & Oram

[57] ABSTRACT

A predetermined number of sectional planes are successively scanned, starting with a sectional plane in an initial position, by shifting a direction of X-ray emission from an X-ray emitting device. A reset operation is effected, after scanning the predetermined number of sectional planes, to switch the direction of X-ray emission to scan a sectional plane in the initial position. An examinee is moved synchronously with the reset operation to set a new sectional plane adjacent the predetermined number of sectional planes to the initial position. A predetermined number of sectional planes are successively scanned, starting with the new sectional plane in the initial position, by shifting the direction of X-ray emission from the X-ray emitting device. After scanning the predetermined number of sectional planes, a reset operation is effected and the examinee is moved to set a new sectional plane adjacent the predetermined number of sectional planes to the initial position. These operations are repeated until all sectional planes are scanned.

10 Claims, 6 Drawing Sheets

METHOD AND APPARATUS FOR COMPUTERIZED TOMOGRAPHY

BACKGROUND OF THE INVENTION

1. Field of the Invention

This invention relates to computerized tomography (CT) for obtaining sectional images of an examinee by emitting X-rays from radial directions to the examinee, and particularly to a method and apparatus for obtaining a plurality of sectional images of an examinee lying still.

2. Description of the Related Art

This type of CT apparatus includes an X-ray emitter and an X-ray detector opposed to each other across an examinee lying still on a top board. X-rays are emitted from radial directions to scan the examinee and collect projection data relating to X-ray absorption in the examinee's body. The data is reversely projected to reconstruct a distribution image of X-ray absorption coefficients in a sectional plane across the examinee's body, thereby to obtain a sectional image of the body. After one slice is scanned, the top board is slid to adjust a next slice of concern of the examinee to a direction of X-ray emission from the X-ray emitter, and a sectional image of this slice is obtained as above.

If a sectional plane has an excessive slice thickness, a virtual image called a partial volume artifact tends to appear in a reconstructed image of, for example, the osseous basal region of brains. In practice, as disclosed in Japanese Patent Publication (Unexamined) No. 61-109551, data of numerous thin slice planes are collected and put to data processing such as addition to obtain a clear image of a thick sectional plane.

However, such a method of obtaining a sectional image has the following disadvantage.

The top board on which an examinee lies is slid at a relatively low speed (about 2 seconds) in order to avoid a displacement between a sectional plane of a site of concern and the X-ray emitter or the like. On the other hand, scanning by the X-ray emitter or the like is carried out at high speed (about 1 second). To collect data of numerous sectional planes under such conditions, sliding of the top board supporting the examinee and scanning by the X-ray emitter or the like must alternately be repeated numerous times. A long time is required to collect data of all of desired sectional planes particularly because of the slow sliding movement of the top board.

SUMMARY OF THE INVENTION

This invention has been made having regard to the state of the art noted above, and its object is, in relation to collection of data of numerous sectional planes with a CT apparatus, to provide a method and apparatus for reducing the time required to collect data of all of required sectional planes.

The above object is fulfilled, according to one aspect of this invention, by a method of obtaining a sectional image of an examinee based on projection data relating to X-ray absorption in sectional planes of the examinee, which data are collected radially of the sectional planes by causing X-ray emitting means and X-ray detecting means opposed to each other across the examinee to scan the sectional planes of the examinee lying still, the method comprising the steps of:

(a) scanning a predetermined number of sectional planes starting with a sectional plane in an initial position by successively shifting a direction of X-ray emission from the X-ray emitting means along a body axis of the examinee;

(b) effecting a reset operation, after scanning the predetermined number of sectional planes, to switch the direction of X-ray emission to scan a sectional plane in the initial position, and moving the examinee synchronously with the reset operation to set a new sectional plane adjacent the predetermined number of sectional planes to the initial position; and (c) repeating the steps (a) and (b) above until all sectional planes are scanned.

A predetermined number of sectional planes are scanned, starting with a sectional plane in the initial position, by successively shifting the direction of X-ray emission from the X-ray emitting means along the body axis of the examinee. A reset operation is effected, after scanning the predetermined number of sectional planes, to switch the direction of X-ray emission to scan a sectional plane in the initial position. The examinee is moved synchronously with the reset operation to set a new sectional plane adjacent the predetermined number of sectional planes to the initial position.

Subsequently, a predetermined number of sectional planes are scanned, starting with the new sectional plane in the initial position, by successively shifting the direction of X-ray emission from the X-ray emitting means along the body axis of the examinee. After scanning the predetermined number of sectional planes, a reset operation is effected and the examinee is moved to set a new sectional plane adjacent the predetermined number of sectional planes to the initial position as above. These operations are repeated until all sectional planes are scanned.

That is, a predetermined number of sectional planes are successively scanned, starting with a sectional plane in the initial position, by shifting the direction of X-ray emission from the X-ray emitting means without moving the examinee. Consequently, the slow movement of the examinee does not occur during scanning of the predetermined number of sectional planes, thereby to achieve a substantial reduction in the time taken in collecting data of all sectional planes. With an increase in the number of sectional planes from which data are collected, the examinee moving time is correspondingly reduced to promote the reduction in processing time.

In a further aspect of this invention, an apparatus for executing the above method is provided, which comprises:

X-ray emitting direction switching means for shifting a direction of X-ray emission from the X-ray emitting means along a body axis of the examinee;

examinee moving means for moving the examinee along the body axis; and control means for effecting a switching control by driving the X-ray emitting direction switching means to shift the direction of X-ray emission from the X-ray emitting means to scan one sectional plane and then a next sectional plane adjacent thereto, thereby to scan successively a predetermined number of sectional planes starting with a sectional plane in an initial position, a reset control by driving the X-ray emitting direction switching means, after scanning the predetermined number of sectional planes, to switch the direction of X-ray emission to scan a sectional plane in the initial position, and a further control by driving the examinee moving means to move the examinee synchronously with the reset control to set a new sectional plane adjacent the predetermined number of sectional planes to the initial position.

For scanning a predetermined number of sectional planes, starting with a sectional plane in the initial position, the control means drives the X-ray emitting direction switching means to shift successively the direction of X-ray emission from the X-ray emitting means along the body axis of the examinee. The control means effects a reset control, after scanning the predetermined number of sectional planes, to drive the X-ray emitting direction switching means to switch the direction of X-ray emission to scan a sectional plane in the initial position. The examinee moving means is driven synchronously with the reset control to move the examinee to set a new sectional plane adjacent the predetermined number of sectional planes to the initial position.

Subsequently, the control means drives the X-ray emitting direction switching means to scan a predetermined number of sectional planes, starting with the new sectional plane in the initial position, by successively shifting the direction of X-ray emission from the X-ray emitting means along the body axis of the examinee. After scanning the predetermined number of sectional planes, the control means effects a reset control and moves the examinee to set a new sectional plane adjacent the predetermined number of sectional planes to the initial position as above. These operations are repeated until all sectional planes are scanned.

That is, a predetermined number of sectional planes are successively scanned, starting with a sectional plane in the initial position, by driving the X-ray emitting direction switching means which is relatively fast, without moving the examinee which is relatively slow. This achieves a substantial reduction in the time taken in collecting data of all sectional planes. With an increase in the number of sectional planes from which data are collected, the examinee moving time is correspondingly reduced to promote the reduction in processing time.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DESCRIPTION OF THE PREFERRED EMBODIMENTS

Preferred embodiments of this invention will be described in detail hereinafter with reference to the drawings.

First Embodiment

Figure 1:
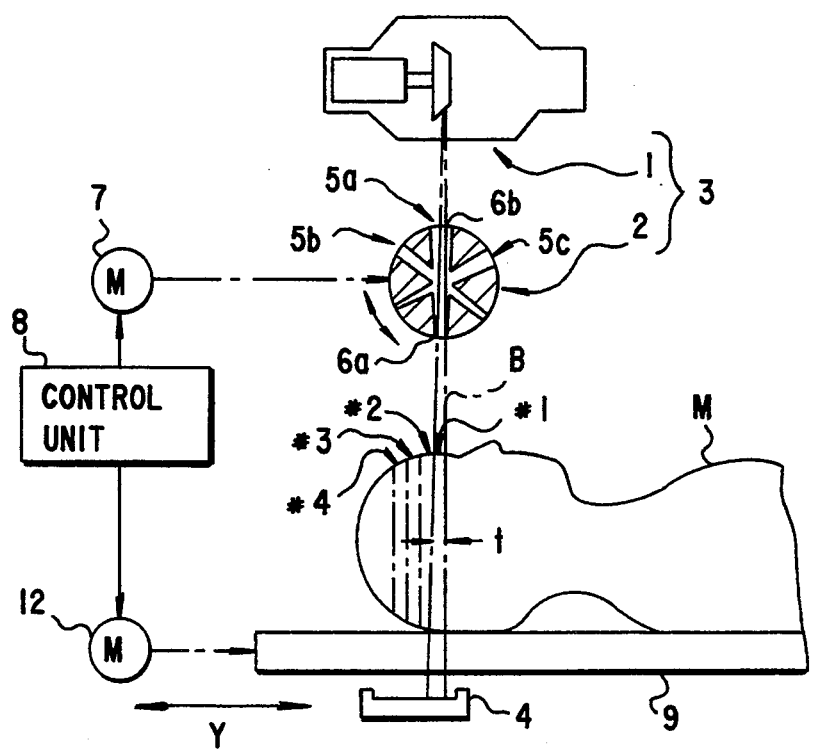
FIG. 1 is a view showing an outline of a CT apparatus embodying this invention.
Figure 2:
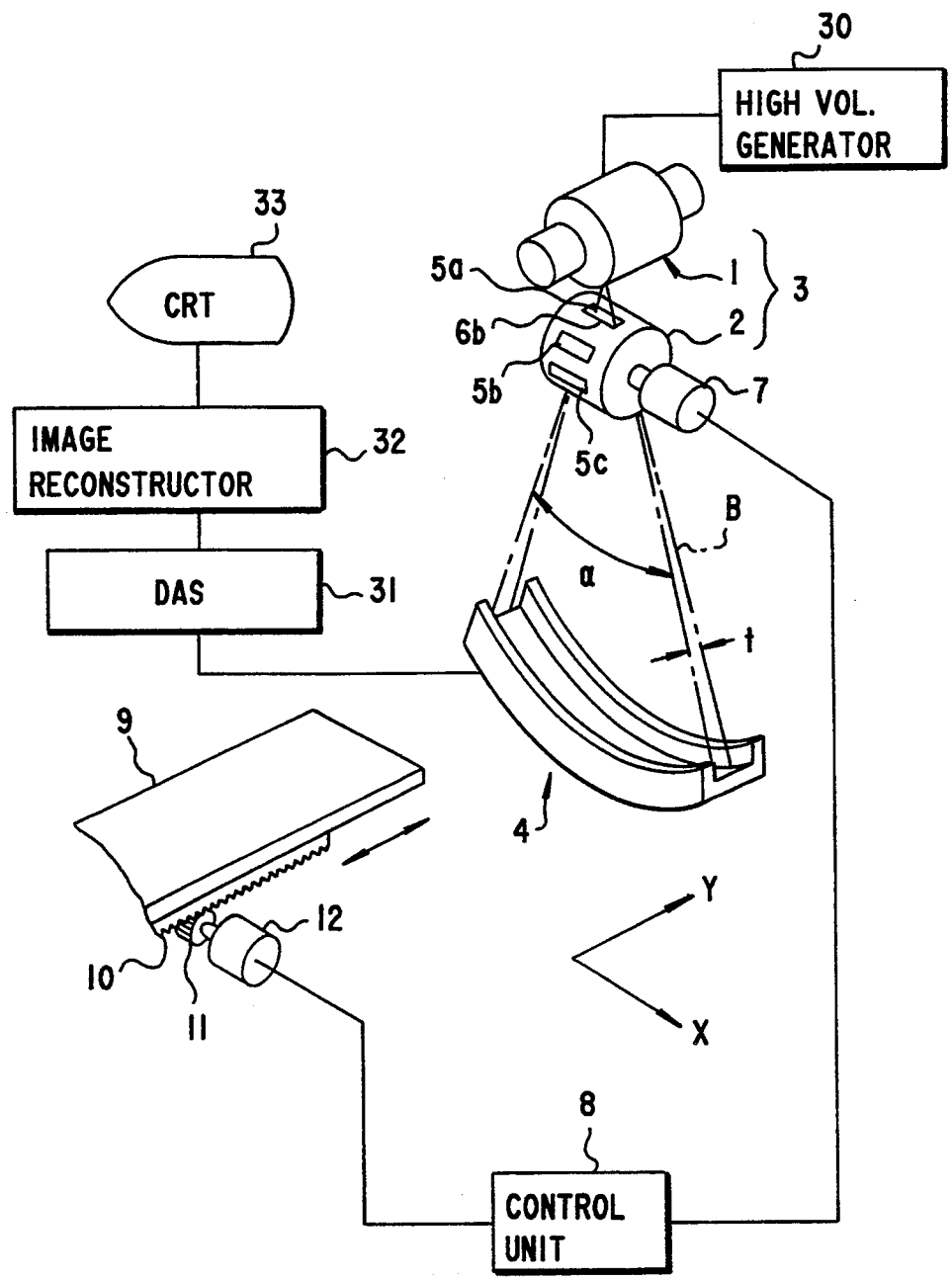
FIG. 2 is a view showing an interior structure and a control system in a first embodiment of this invention.

FIG. 1 is a view showing an outline of a CT apparatus in a first embodiment of this invention. FIG. 2 is a view showing an interior structure and a control system of the first embodiment.

An X-ray tube 1 and an X-ray collimator 2 constitute an X-ray emitting device 3 secured to an inner peripheral surface of a rotary frame mounted in an opening of a gantry not shown. An X-ray detector 4 is secured to the rotary frame opposite the X-ray emitting device 3 to detect transmitted X-rays and produce electric signals corresponding thereto. The rotary frame is rotatable around an examinee M lying on a top board 9 and inserted into the gantry opening. Consequently, the X-ray emitting device 3 and X-ray detector 4 revolve in an opposed relationship to each other to scan sectional planes of concern of the examinee M.

The X-ray tube 1 acting as an X-ray emitting means is connected to a high voltage generator 30 which supplies thereto a high voltage necessary for X-ray generation. The X-ray detector 4 has a data acquisition system (DAS) 31 for receiving detection signals and converting these signals into digital signals, an image reconstructor 32 for reconstructing sectional images based on the digital signals received, and a CRT 33 for displaying the reconstructed sectional images.

The X-ray collimator 2 is disposed adjacent the X-ray tube 1 to adjust a slice thickness and diverging angle of X-rays emitted from the X-ray tube 1. The X-ray collimator 2 is formed of an X-ray shielding material such as brass or lead to have a cylindrical shape. The X-ray collimator 2 defines a slit 5a extending in X direction which is a direction of divergence of the X-rays emitted. (Y direction perpendicular to X direction corresponds to the axial direction of examinee M.) The X-rays entering the slit 5a exit through a slot 6a having a circumferential dimension determining a slice thickness "t", and a dimension in X direction determining a diverging angle $\alpha$ of the X-rays. A slot 6b defining an X-ray incidence port has a larger circumferential dimension than the slot 6a, and the same dimension in X direction as the slot 6a, wherefore the slit 5a is wedge-shaped. Thus, X-rays emitted from the X-ray tube 1 enter the slit 5a through the slot 6b and converge in departing from the slot 6a to form an X-ray beam B having a desired shape. To provide varied slice thicknesses, the X-ray collimator 2 defines, besides the slit 5a, a plurality of slits 5b and 5c arranged circumferentially thereof and having different opening dimensions in the circumferential direction.

The X-ray collimator 2 has an axis extending in X direction, with an output shaft of a reversible drive motor 7 attached to one axial end thereof, the other end being attached to the rotary frame in the gantry opening through a bearing not shown. Thus, the X-ray collimator 2 is rotatable about its axis with rotation of the drive motor 7. Not only is it possible to select one of the slits 5a–5c but the slit 5a, for example, may be minutely shifted to swing the X-ray beam B, as converged through the slot 6a, in Y direction. Even with a shift of the slit 5a, the slot 6b having a large circumferential dimension can direct X-rays emitted from the X-ray tube 1 into the slit 5a. The rotation of the X-ray collimator 2, i.e. reversible rotation of the drive motor 7, is controlled by a control unit 8. The X-ray collimator 2 corresponds to the X-ray emitting direction switching means of this invention.

The control unit 8 controls movement of the top board 9 supporting the examinee M besides the rotation of the X-ray collimator 2. The top board 9 includes a rack 10 extending longitudinally thereof, and a pinion 11 meshed with the rack 10. An output shaft of a reversible drive motor 12 is attached to the pinion 11. The pinion 11 is rotatable with rotation of the drive motor 12 to slide the top board 9 longitudinally (in Y direction) through the rack 10. The reversible rotation of the drive motor 12 is controlled by the control unit 8. The top board 9 corresponds to the examinee moving means of this invention.

The control unit 8 comprises, for example, a microcomputer including a CPU (central processing unit), a CPU memory, a ROM (read-only memory) and the like. A sequence (program) of collecting data for sectional images, which will be described later, is stored in the ROM, and the CPU carries out processing according to the program. The CPU memory is used for temporarily storing data being processed. The control unit 8 corresponds to the control means of this invention.

The X-ray detector 4 is in the form of a curved band and attached to the rotary frame in the gantry opening as noted hereinbefore. The X-ray detector 4 has a dimension in X direction to detect all X-rays diverging in X direction through the slit 5a (5b or 5c) and transmitted through the examinee M. Its dimension in Y direction is one to detect all X-rays when the X-ray collimator 2 is minutely rotated to photograph a plurality of (n) sectional images. The "n" is the number of sectional planes to be scanned by X-rays whose emitting direction is shifted in Y direction by the control unit 8 as described hereinafter.

Figure 3:
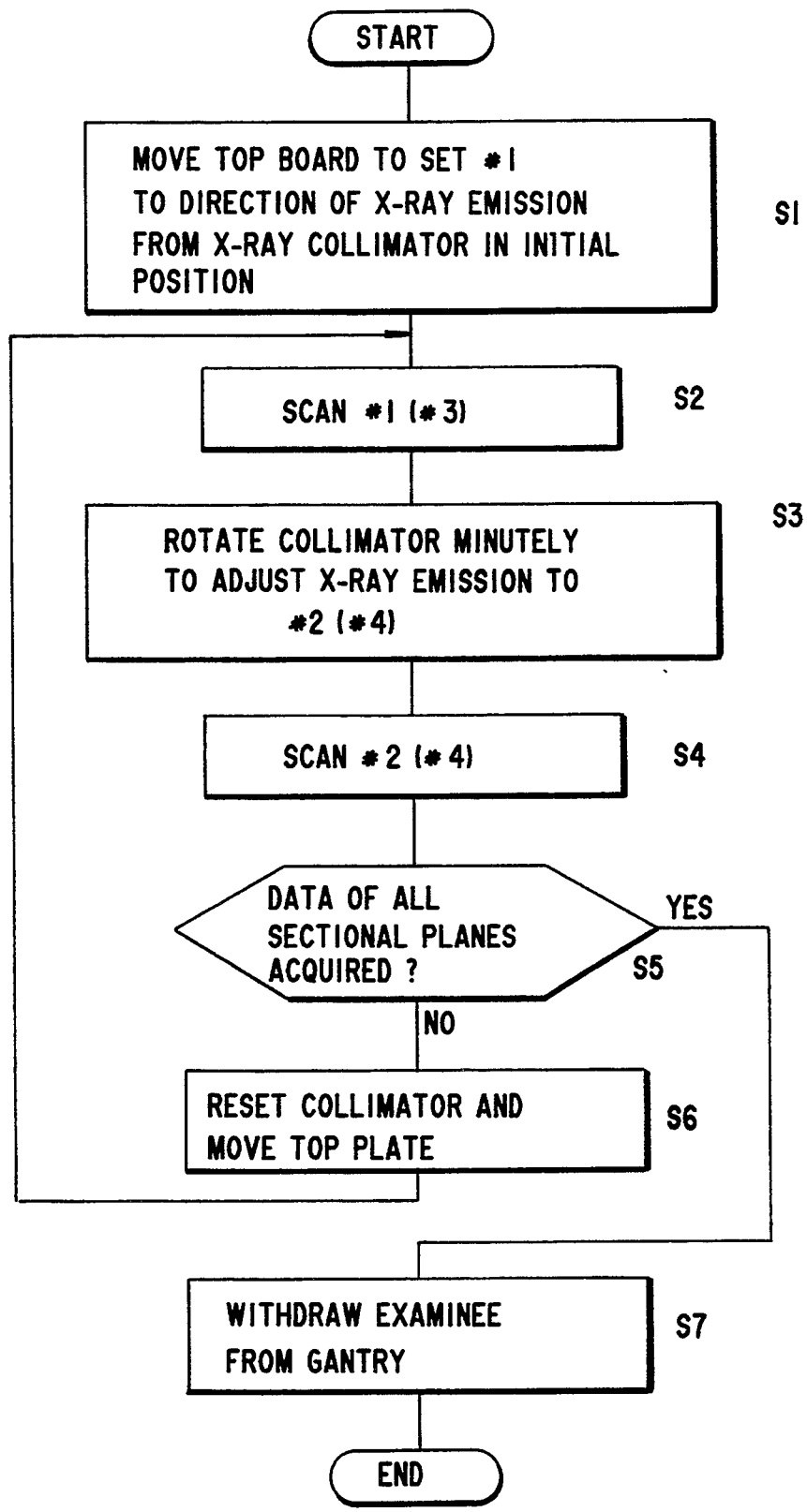
FIG. 3 is a flowchart showing a sequence of collecting data of sectional planes in the first embodiment.

The sequence of collecting data of sectional images with the CT apparatus having the above construction will be described next with reference to the flowchart shown in FIG. 3. In this sequence, as shown in FIG. 1, sectional planes #1 to #4 of the examinee M are scanned one after another. The sectional planes #1 to #4 are close to one another and each has a 2 mm slice thickness.

The control unit 8 moves the top board 9 supporting the examinee M to adjust the first sectional plane #1 to a position to which the X-ray beam B travels vertically from the X-ray collimator 2 (the position at this time of slit 5a in the X-ray collimator 2 being called an initial position) (step S1). In this state, the X-ray emitting device 3 and X-ray detector 4, as opposed to each other, are revolved around the examinee M to scan the sectional plane #1 (step S2). When the sectional plane #1 has been scanned, the control unit 8 minutely rotates the X-ray collimator 2 to shift X-rays 2 mm in Y direction to irradiate the next sectional plane #2 (step S3). In this state, the X-ray emitting device 3 and X-ray detector 4, as opposed to each other, are revolved around the examinee M to scan the sectional plane #2 (step S4). Although the X-rays are not perpendicular to Y direction at this time, no problem arises in image reconstruction since the sectional plane is scanned with one revolution thereof so that the center of irradiation of the X-rays with respect to the sectional plane is substantially perpendicular to Y direction. When the sectional plane #2 has been scanned, the control unit 8 rotates the X-ray collimator 2 back to the initial position (i.e. resets the collimator 2), shifting the X-rays −2 mm in Y direction, to scan sectional planes #3 and #4. Simultaneously with the reset operation, the control unit 8 starts an operation to move the top board 9 to adjust the sectional plane #3 to the initial position (steps S5 and S6). The sectional planes #3 and #4 are scanned as at steps S2 through S4 in place of sectional planes #1 and #2. When data of all the sectional planes #1 through #4 have been collected, the top board 9 is driven to withdraw the examinee M from the gantry (step S7).

Where other sectional planes #5, #6 and so on are to be photographed, steps S2–S6 are repeated to scan two sectional planes by minutely rotating the X-ray collimator 2, and the top board 9 (examinee M) is moved each time two sectional planes have been scanned. In this way, data of numerous sectional planes may be collected. It is also possible to scan sectional planes #1–#3 first by minutely rotating the X-ray collimator 2, and move the top board 9 each time three sectional planes have been scanned. In this case, however, the X-ray detector 4 must have a sufficient dimension in Y direction to allow scanning of sectional planes #1–#3. Where, for example, the CT apparatus is capable of scanning a 10 mm slice thickness, a site of concern is divided into sectional planes each having a 2 mm thickness to be scanned. The resulting data are processed to form a sectional image of 10 mm slice thickness free of a partial volume artifact. In this sequence, therefore, the X-ray collimator 2 may be minutely rotated five times to effect a 2 mm shift in Y direction each time.

The time taken in collecting data in the above sequence will be described with reference to the time chart shown in FIG. 4.

Figure 4:
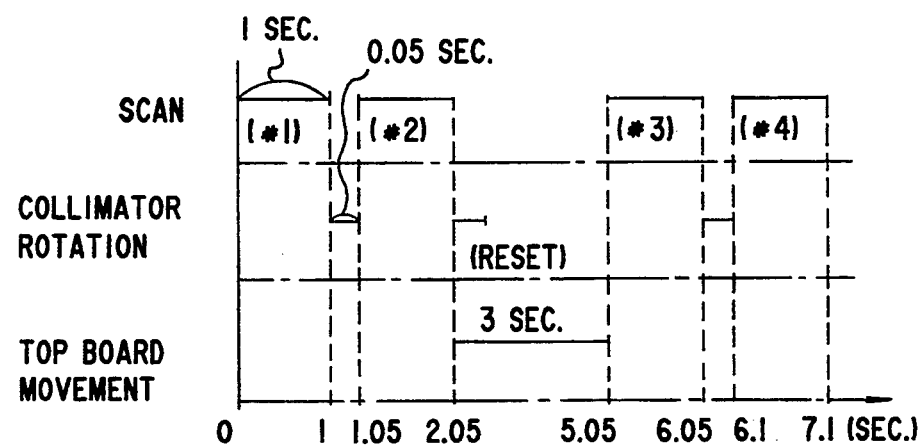
FIG. 4 is a time chart showing processing time taken in data collection in the first embodiment.

As seen from FIG. 4, assuming that step S1 is completed at a point of time "0", the scanning of sectional plane #1 (step S2) consumes about 1 second, then the rotation of X-ray collimator 2 (step S3) about 0.05 second, and the scanning of sectional plane #2 about 1 second. Next, the resetting rotation of X-ray collimator 2 (about 0.05 second) is started simultaneously with the movement of top board 9 (about 3 seconds) (step S6). The resetting rotation of X-ray collimator 2 is finished during the movement of top board 9. Thereafter, the scanning of sectional plane #3 (step S2) consumes about 1 second, then the rotation of X-ray collimator 2 (step S3) about 0.05 second, and the scanning of sectional plane #4 about 1 second. The time consumed up to completion of the scanning of sectional plane #4 is 1+0.05+1+3+1+0.05+1 which is about 7.1 seconds. The movement of top board 9 is regarded as consuming about 3 seconds since moving the sectional plane #3 to the position of sectional plane #1 (4 mm) in one stroke is considered to consume a longer time than a 2 mm movement as described later.

Next, the time taken in collecting data with a conventional apparatus will be described with reference to the time chart shown in FIG. 5.

Figure 5:
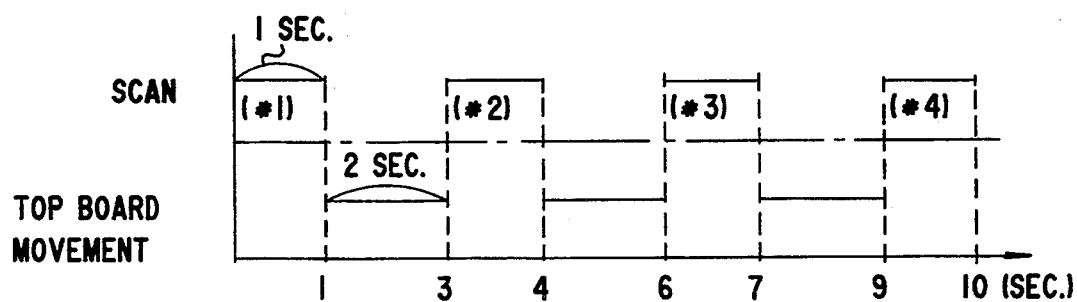
FIG. 5 is a time chart showing processing time taken in data collection with a conventional apparatus.

As seen from FIG. 5, assuming that the sectional plane #1 is set to a scan position (corresponding to step S1 above) at a point of time "0", the scanning of sectional plane #1 consumes about 1 second, and then about 2 seconds are consumed in moving the top board 9 to set the sectional plane #2 to the scan position. Next, about 1 second is consumed in scanning the sectional plane #2, about 2 seconds in moving the top board 9 to set the sectional plane #3 to the scan position, about 1 second in scanning the sectional plane #3, about 2 seconds in moving the top board 9 to set the sectional plane #4 to the scan position, and finally about 1 second in scanning the sectional plane #4. Thus, the time consumed up to completion of the scanning of sectional plane #4 is 1+2+1+2+1+2+1 which is about 10 seconds. The movement of top board 9 is regarded as consuming about 2 seconds since this is a 2 mm movement.

A comparison between FIG. 4 and FIG. 5 shows that the time needed to collect the data of sectional planes #1–#4 has been reduced by as much as about 2.9 (10–7.1) seconds. In collecting the data of sectional planes #1–#6, for example, this embodiment takes about 12.15 (7.1+3+1+0.05+1) seconds whereas the conventional apparatus takes about 16 (10+2+1+2+1) seconds. Thus, the larger the number of sectional planes scanned is, the more processing time is saved by omitting the movement of top board 9, which promotes the processing time reduction.

Second Embodiment

Figure 6:
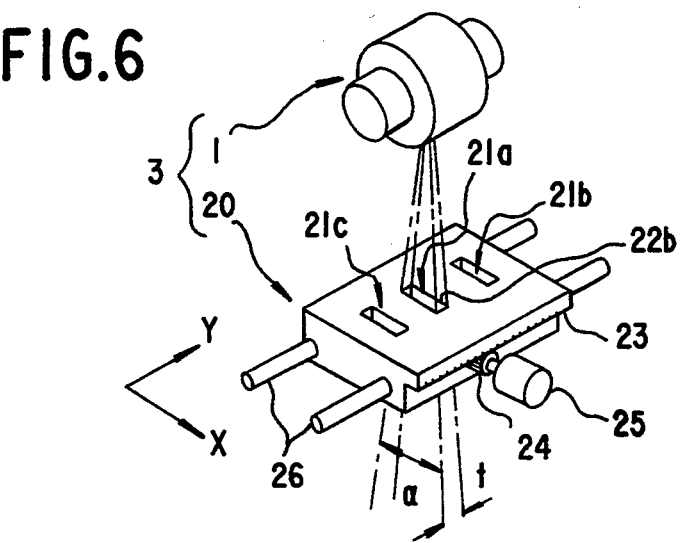
FIG. 6 is a perspective view of an X-ray collimator in a second embodiment of this invention.

A second embodiment will be described next with reference to FIG. 6, which employs a different X-ray collimator to swing X-rays in Y direction.

This X-ray collimator 20 is penetrated and slidably supported by parallel support shafts 26 extending in Y direction. These support shafts 26 are fixed to inner walls of a rotary frame mounted in a gantry opening. The X-ray collimator 20 is formed of an X-ray shielding material such as brass or lead to have a plate shape, and defines slits 21a–21c extending in a diverging direction of X-rays. Each of the slits 21a–21c has dimensions to provide a diverging angle α and slice thickness "t" of the X-rays. The slit 21a, for example, is wedge-shaped with a slot 22b defining an X-ray incidence port thereof and having a larger dimension in Y direction than a slot 22a (not seen in FIG. 6) defining an exit port. The X-ray collimator 20 is slidable in Y direction by a drive mechanism described hereunder.

The X-ray collimator 20 includes a rack 23 extending in Y direction, and a pinion 24 meshed with the rack 23. An output shaft of a reversible drive motor 25 is attached to the pinion 24. The pinion 24 is rotatable with rotation of the drive motor 25 to reciprocate the rack 23 in Y direction. The rotation of the drive motor 25 is controlled by a control unit, not shown, similar to the control unit 8 in the first embodiment. The movement of a top board is also controlled by the control unit.

The other details of this embodiment may be the same as in the first embodiment. Following the sequence described with reference to FIG. 3, data of a plurality of sectional planes may be collected with the reciprocating movement in Y direction of the X-ray collimator 20 replacing the rotation of the X-ray collimator 2 at steps S3 and S6.

Third Embodiment

A third embodiment of this invention will be described next.

In each of the first and second embodiments, the X-ray collimator 2 or 20 is rotatable or reciprocable to shift the X-ray emitting direction. In the third embodiment, the X-ray emitting device 3 including the X-ray tube 1 and X-ray collimator 2 or 20 is arranged slidable axially of the examinee M (in Y direction).

Figure 7:
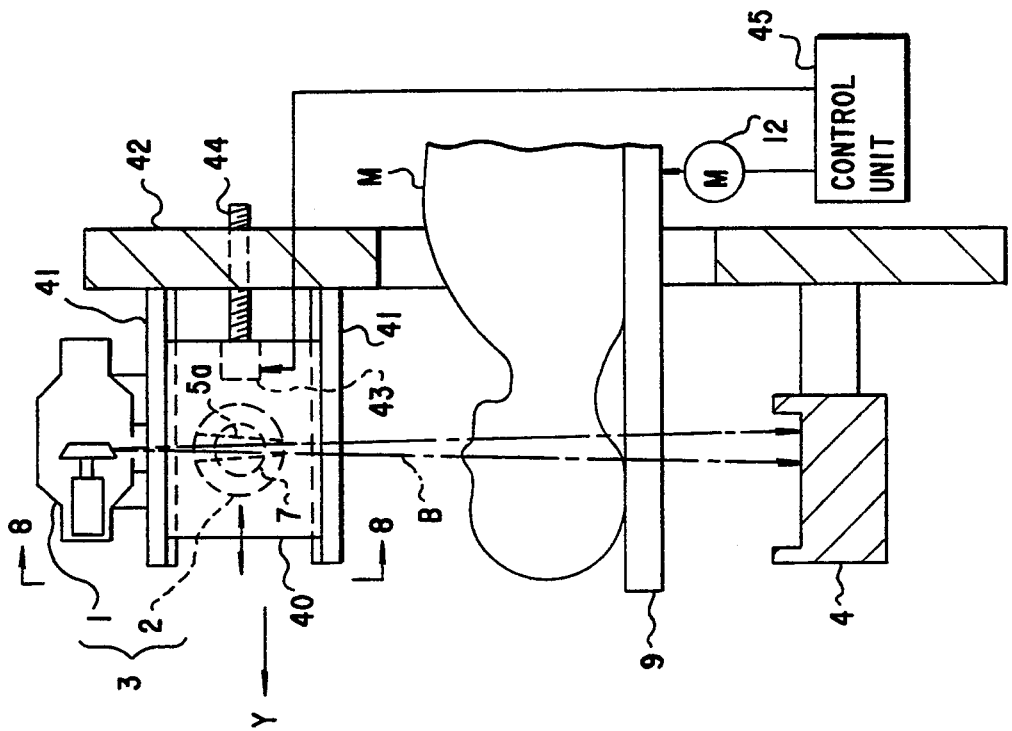
FIG. 7 is a view showing a third embodiment of this invention.
Figure 8:
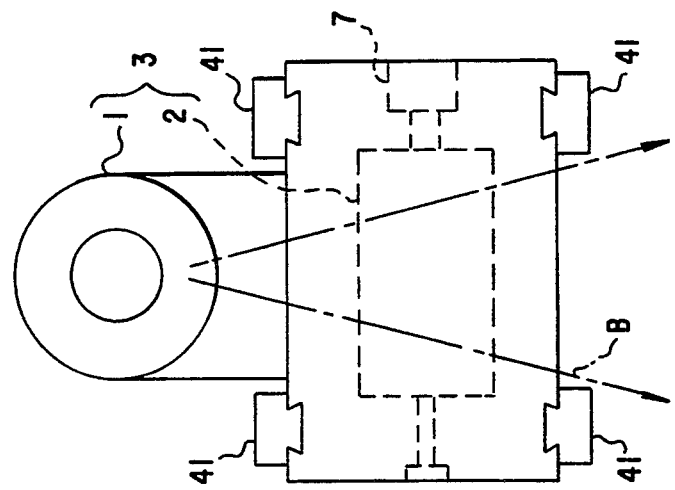
FIG. 8 is a section taken on line 8—8 of FIG. 7.

A specific construction will be described with reference to FIGS. 7 and 8. FIGS. 7 and 8 depict a cylindrical X-ray collimator 2 as described in the first embodiment, and this embodiment will be described hereinafter using this collimator 2 as an example. Like reference numerals are used to identify like parts in FIGS. 1 and 2 which are the same as in the first embodiment and will not be described again.

The X-ray collimator 2 is rotatably mounted in a case 40, with the X-ray tube 1 fixed to the top of the case 40, so that the X-ray tube 1 and X-ray collimator 2 are movable together. The case 40 has an upper surface and a lower surface including X-ray penetrable windows not shown. X-rays emitted from the X-ray tube 1 travel through the X-ray penetrable window in the upper surface of the case 40 into the slit 5a of the X-ray collimator 2. An X-ray beam B exiting the slit 5a travels through the X-ray penetrable window in the lower surface of the case 40 to the examinee M.

The case 40 is supported by four slide rails 41 fixed to a rotary frame 42 rotatably mounted in a gantry. The case 40 includes a motor 43 for reversibly rotating a screw shaft 44 meshed with the rotary frame 42.

The screw shaft 44 is rotatable with rotation of the motor 43 to slide the case 40 containing the X-ray collimator 2, together with the X-ray tube 1, in Y direction along the slide rails 41. The rotation of the motor 43 is controlled, as is the motor 12 for moving the top board 9, by a control unit 45 similar to the control unit 8 in the first embodiment. An X-ray detector 4 is attached to the rotary frame 42 in an opposed relationship to the X-ray emitting device 3.

For scanning sectional planes, the X-ray collimator 2 is first rotated to select a desired slit. At this time, the X-ray collimator 2 is rotated to a position to allow the X-ray beam B exiting the slit to travel perpendicular to Y direction. In this state, the control unit 45 rotates the motor 43 to move the X-ray emitting device 3 to an initial position, and at the same time moves the top board 9 to set a first sectional plane of the examinee M to the initial position.

After the first sectional plane is scanned, the control unit 45 rotates the motor 43 to slide the X-ray emitting device 3 in Y direction for enabling scanning of a sectional plane adjacent the first sectional plane scanned. In this way, a desired number of sectional planes are scanned by sliding the X-ray emitting device 3 in Y direction. Subsequently, the control unit 45 effects a reset control to rotate the motor 43 backward to return the X-ray emitting device 3 to the initial position. At the same time, the top board 9 is moved to set a next sectional plane to be scanned, adjacent the scanned sectional planes, to the initial position.

This sectional plane and adjacent sectional planes are successively scanned by moving the X-ray emitting device 3 in Y direction as above. After a desired number of sectional planes are scanned by sliding the X-ray emitting device 3 in Y direction, the control unit 45 effects the reset control and moves the top board 9 to set a next sectional plane to be scanned to the initial position.

The above operations are thereafter repeated until completion of data collection. With the X-ray emitting device 3 arranged slidable in Y direction as described above, the time taken in sliding the X-ray emitting device 3 in Y direction is shorter than the time taken in moving the top board 9. Consequently, as in the first and second embodiments, data collection requires a reduced processing time. Moreover, in the third embodiment, the X-rays are emitted perpendicular to Y direction for all sectional planes scanned after sliding the X-ray emitting device 3 in Y direction.

The X-ray collimator mounted in the case 40 is not limited to the cylindrical collimator, but may be the plate-shaped X-ray collimator 20 (see FIG. 6) described in the second embodiment.

Fourth Embodiment

Figure 9:
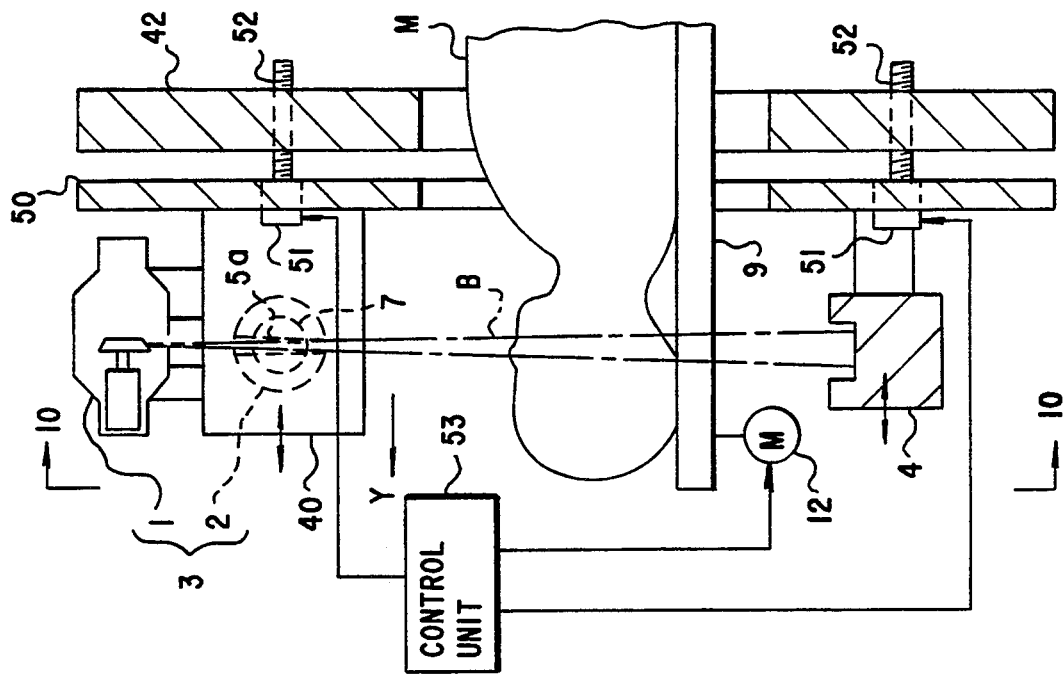
FIG. 9 is a view showing a fourth embodiment of this invention.
Figure 10:
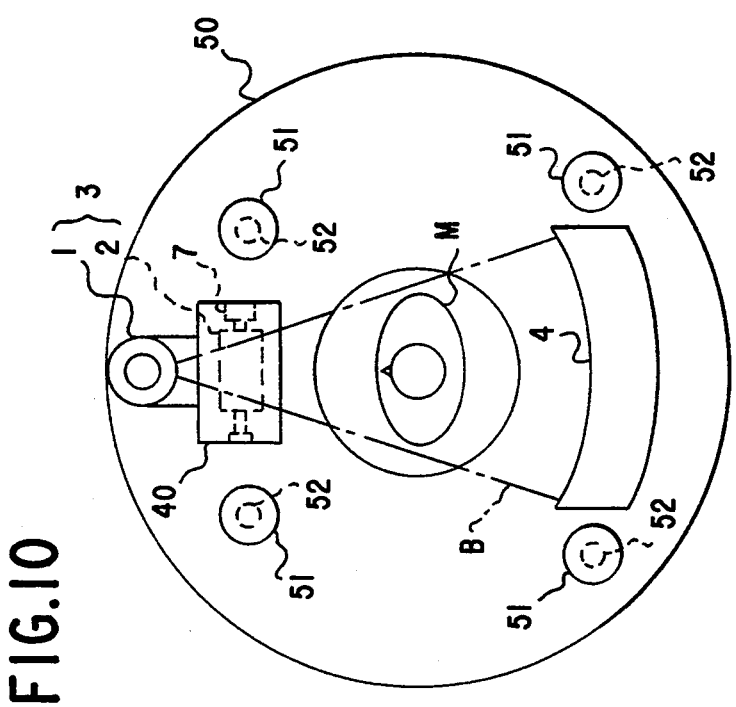
FIG. 10 is a section taken on line 10—10 of FIG. 9.

A fourth embodiment of this invention will be described next with reference to FIGS. 9 and 10.

The fourth embodiment is characterized in that the X-ray emitting device 3 and X-ray detector 4 are synchronously slidable in Y direction. Like reference numerals are used to identify like parts in FIGS. 1, 2, 7 and 8 which are the same as in the first and third embodiments and will not be described again.

Specifically, the X-ray emitting device 3 and X-ray detector 4 are movable in Y direction together, with a case 40 having an X-ray tube 1 fixed thereto and an X-ray collimator 2 rotatably mounted therein, and the X-ray detector 4, being attached to a support ring 50 in an opposed relationship with each other. The support ring 50 includes four motors 51 for rotating screw shafts 52 meshed with a rotary frame 42. The motors 51 are synchronously rotatable to slide the X-ray emitting device 3 and X-ray detector 4 in Y direction by means of the support ring 50. The respective motors 51 are controlled to rotate synchronously by a control unit 53 similar to the control unit 8 in the first embodiment. This control unit 53 also controls a motor 12 for moving a top board 9.

With this construction, as in the third embodiment, a desired number of sectional planes may be scanned by sliding the X-ray emitting device 3 and X-ray detector 4 in Y direction to reduce the processing time for data collection. Further, in the fourth embodiment, as in the third embodiment, the X-rays are emitted perpendicular to Y direction for all sectional planes scanned after sliding the X-ray emitting device 3 in Y direction. The X-ray detector 4 in the fourth embodiment may have a width in Y direction just enough to enable scanning of one sectional plane.

The X-ray collimator mounted in the case 40 is not limited to the cylindrical collimator, but may be the plate-shaped X-ray collimator 20 (see FIG. 6) described in the second embodiment.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method of obtaining sectional images of a plurality of sectional planes adjacent one another in a direction along a body axis of an examinee, by repeating a process of obtaining one sectional image based on projection data relating to X-ray absorption in each sectional plane of the examinee, which data are collected by X-ray detecting means radially of the sectional plane by causing X-ray emitting means and the X-ray detecting means opposed to each other across the examinee to revolve around the body axis of the examinee lying still, while causing the X-ray emitting means to emit X-rays toward each sectional plane to scan the sectional plane, said method comprising the steps of:

(a) scanning a group of sectional planes successively from a first sectional plane set to an initial position to a last sectional plane in said group, by causing said X-ray emitting means to emit X-rays toward each sectional plane, thereby scanning each sectional plane of the examinee lying still within a direction of X-ray emission fixed during one scan, the direction of X-ray emission being shifted for each successive scan;

(b) effecting a reset operation, after scanning the last sectional plane in said group, to switch the direction of X-ray emission to scan a sectional plane to be set to said initial position, and moving said examinee synchronously with said reset operation and in a direction in which said direction of X-ray emission is switched in said reset operation, to set to said initial position a new first sectional plane adjacent said last sectional plane in said group having been scanned; and (c) repeating the steps (a) and (b) above until completion of scanning of a predetermined number of sectional planes adjacent one another along the body axis of the examinee.

2. An apparatus for obtaining sectional images of a plurality of sectional planes adjacent one another in a direction along a body axis of an examinee, by repeating a process of obtaining one sectional image based on projection data relating to X-ray absorption in each sectional plane of the examinee, which data are collected by X-ray detecting means radially of the sectional plane by causing X-ray emitting means and the X-ray detecting means opposed to each other across the examinee to revolve around the body axis of the examinee lying still while causing the x-ray emitting means to emit X-rays toward each sectional plane to scan the sectional plane, said apparatus comprising:

(a) X-ray emitting direction switching means for shifting a direction of X-ray emission from said X-ray emitting means along the body axis of the examinee;

(b) examinee moving means for moving said examinee along said body axis; and (c) control means for repeatedly effecting, until completion of scanning of a predetermined number of sectional planes adjacent one another along the body axis of the examinee, a scanning control by driving said X-ray emitting direction switching means to shift the direction of X-ray emission from said X-ray emitting means to scan a group of sectional planes successively from a first sectional plane set to an initial position to a last sectional plane in said group, said X-ray emitting means emitting X-rays toward each sectional plane, thereby scanning each sectional plane of the examinee lying still with the direction of X-ray emission fixed during one scan, the direction of X-ray emission being shifted for each successive scan, a reset control by driving said X-ray emitting direction switching means, after scanning the last sectional plane in said group, to switch the direction of X-ray emission to scan a sectional plane to be set to said initial position, and an examinee moving control by driving said examinee moving means to move said examinee synchronously with said reset control and in a direction in which said direction of X-ray emission is switched in said rest control, to set to said initial position a new first sectional plane adjacent said last sectional plane in said group having been scanned.

3. An apparatus as defined in claim 2, wherein said X-ray emitting direction switching means includes an X-ray collimator rotatable axially of said examinee, said control means being operable to rotate said X-ray collimator axially of said examinee to shift the direction of X-ray emission, thereby to direct X-rays to each sectional plane in said group of sectional planes scanned in said scanning control, and effecting said reset control.

4. An apparatus as defined in claim 3, wherein said X-ray collimator has a cylindrical shape and includes a plurality of slits arranged circumferentially thereof to adjust a slice width and diverging angle of X-rays emitted from said X-ray emitting means.

5. An apparatus as defined in claim 4, wherein said slits are wedge-shaped, each with an incidence port for receiving the X-rays emitted from said X-ray emitting means having a larger circumferential width than an exit port for delivering the X-rays.

6. An apparatus as defined in claim 2, wherein said X-ray emitting direction switching means includes an X-ray collimator slidable axially of said examinee, said control means being operable to slide said X-ray collimator axially of said examinee to shift the direction of X-ray emission, thereby to direct X-rays to each sectional plane in said group of sectional planes scanned in said scanning control, and effecting said rest control.

7. An apparatus as defined in claim 6, wherein said X-ray collimator has a plate-like shape and includes a plurality of slits arranged axially of said examinee to adjust a slice width and diverging angle of X-rays emitted from said X-ray emitting means.

8. An apparatus as defined in claim 7, wherein said slits are wedge-shaped, each with an incidence port for receiving the X-rays emitted from said X-ray emitting means having a larger width than an exit port for delivering the X-rays.

9. An apparatus as defined in claim 2, wherein said X-ray emitting direction switching means includes a mechanism for shifting said X-ray emitting means axially of said examinee, said control means being operable to shift said X-ray emitting means axially of said examinee to shift the direction of X-ray emission, thereby to direct X-rays to each sectional plane in said group of sectional planes scanned in said scanning control, and effecting said reset control.

10. An apparatus as defined in claim 9, wherein said X-ray detecting means is shiftable with said X-ray emitting means axially of said examinee, said control means being operable to shift said X-ray emitting means and said X-ray detecting means axially of said examinee to shift the direction of X-ray emission, thereby to direct X-rays to each sectional plane in said group of sectional planes scanned in said scanning control, and effecting said reset control.

* * * * *